(12) United States Patent
Zhong (10) Patent No.: US 10,213,136 B2
(45) Date of Patent: Feb. 26, 2019

(54) METHOD FOR SENSOR ORIENTATION INVARIANT GAIT ANALYSIS USING GYROSCOPES

(71) Applicant: BAE Systems Information and Electronic Systems Integration Inc., Nashua, NH (US)

(72) Inventor: Yu Zhong, Winchester, MA (US)

(73) Assignee: BAE Systems Information and Electronic Systems Integration Inc., Nashua, NH (US)

(*) Notice: Subject to any disclaimer, the term of this patent is extended or adjusted under 35 U.S.C. 154(b) by 687 days.

(21) Appl. No.: 14/865,677

(22) Filed: Sep. 25, 2015

(65) Prior Publication Data

US 2016/0192863 A1 Jul. 7, 2016

Related U.S. Application Data

(60) Provisional application No. 62/055,267, filed on Sep. 25, 2014.

(51) Int. Cl.
*A61B 5/00* (2006.01)
*A61B 5/11* (2006.01)
*A61B 5/117* (2016.01)

(52) U.S. Cl.
CPC ........... *A61B 5/112* (2013.01); *A61B 5/117* (2013.01); *A61B 5/1118* (2013.01); *A61B 5/7264* (2013.01); *A61B 5/7271* (2013.01); *A61B 2505/09* (2013.01); *A61B 2562/0219* (2013.01)

(58) Field of Classification Search
CPC ......... A61B 5/11; A61B 5/112; A61B 5/1121; A61B 5/1122; A61B 5/0022; A61B 5/1038; A61B 5/6895; A61B 5/7271; A61B 5/1118; A61B 5/117
See application file for complete search history.

(56) References Cited

U.S. PATENT DOCUMENTS

| | | | |
|---|---|---|---|
| 8,109,890 B2* | 2/2012 | Kamiar | A61B 5/1038 600/595 |
| 8,876,739 B2* | 11/2014 | Salarian | A61B 5/4023 600/595 |
| 8,930,163 B2 | 1/2015 | Kordari et al. | |
| 9,801,568 B2* | 10/2017 | Ziaie | A61B 5/112 |
| 2010/0280792 A1 | 11/2010 | Paiva Velhote Correia et al. | |
| 2012/0144916 A1 | 6/2012 | Doheny et al. | |
| 2013/0131555 A1 | 5/2013 | Hook et al. | |
| 2014/0032165 A1 | 1/2014 | Sarrafzadeh et al. | |

OTHER PUBLICATIONS

Manon Kok, Jeroen Hol, Thomas Schon, An optimization-based approach to human body motion capture using inertial sensors, 2014, In Proceedings of the 19th IFAC World Congress, 2014, 79-85. ISBN: 978-3-902823-62-5.

(Continued)

*Primary Examiner* — Max Hindenburg
(74) *Attorney, Agent, or Firm* — Maine Cernota & Rardin (57) ABSTRACT

A method for invariant gait analysis using gyroscope data wherein the improvement comprises the step of using pairs of raw measurements to factor out orientation, wherein a motion representation which is both invariant to sensor orientation changes and highly discriminative to enable high-performance gait analysis.

20 Claims, 6 Drawing Sheets

FLOW CHART

(56) References Cited

OTHER PUBLICATIONS

T. Liu, Y. Inoue, and K. Shibata. "Development of a wearable sensor system for quantitative gait analysis." Measurement 42, No. 7 (2009): 978-988.
J. Mantyjarvi, J. Himberg, and T. Seppanen. Recognizing human motion with multiple acceleration sensors, IEEE Int'l Conf. Systems, Man, and Cybernetics, 2001.
J. Mantyjarvi, M. Lindholm, E. Vildjiounaite, S.-M. Makela, and H. Ailisto, Identifying users of portable devices from gait pattern with accelerometers, IEEE Int'l Conf. Acoustics, Speech, and Signal Processing, vol. 2, pp. 973-976, 2005.
R. E. Mayagoitia, A. V. Nene, and P. H. Veltink. "Accelerometer and rate gyroscope measurement of kinematics: an inexpensive alternative to optical motion analysis systems." Journal of biomechanics 35, No. 4 (2002): 537-542.
B. Najafi, K. Aminian, F. Loew, Y. Blanc, and P. A. Robert, Measurement of stand-sit and sit-stand transitions using a miniature gyroscope and its application in fall risk evaluation in the elderly. Biomedical Engineering, IEEE Transactions on, 49(8), 843-851, (2002).
G. Pan, Y. Zhang, and Z. Wu. Accelerometer-based gait recognition via voting by signature points. Electronics letters 45.22 (2009): 1116-1118.
W. Premerlani and P. Bizard, Direction cosine matrix IMU: theory. http://gentlenav.googlecode.com/files/DCMDraft2.pdf 2009.
N. Ravi, N. Dandekar, P. Mysore, andM.L. Littman, Activity recognition from accelerometer data. In AAAI (pp. 1541-1546), 2005.
A. Salarian, H. Russmann, F. J. Vingerhoets, C. Dehollaini, Y. Blanc, P. R. Burkhard, and K Aminian. Gait assessment in Parkinson's disease: toward an ambulatory system for long-term monitoring. Biomedical Engineering, IEEE Transactions on, 51(8), 1434-1443, (2004).
A. Sabatini, M. Angelo, C. Martelloni, S. Scapellato, and F. Cavallo. "Assessment of walking features from foot inertial sensing." Biomedical Engineering, IEEE Transactions on 52, No. 3 (2005): 486-494.
S. Sarkar, P. J. Phillips, Z. Liu, I. R. Vega, P.Grother, and K. W. Bowyer, The humanid gait challenge problem: Data sets, performance, and analysis. IEEE Trans.Pattern Analysis and Machine Intelligence, 27(2):162-177, 2005.
T. Shany, S. J. Redmond, M., R. Narayanan, and N. H. Lovell. "Sensors-based wearable systems for monitoring of human movement and falls." Sensors Journal, IEEE 12, No. 3 (2012): 658-670.
S. Sprager, A cumulant-based method for gait identification using accelerometer data with principal component analysis and support vector machine, in Sensors, Signals, Visualization, Imaging, Simulation and Materials, pp. 94-99, 2009.
K. Tong, M. H. Granat. "A practical gait analysis system using gyroscopes." Medical engineering & physics 21, No. 2 (1999): 87-94.
N. T. Trung, Y. Makihara, H. Nagahara, Y. Mukaigawa, and Y. Yagi., Performance evaluation of gait recognition using the largest inertial sensor-based gait database, 5th IAPR International Conference on Biometrics (ICB), pp. 360-366, 2012.
O. Woodman. An introduction to inertial navigation. Technical Report 696, University of Cambridge, 2007.
F. Juefei-Xu, C. Bhagavatula, A. Jaech, U. Prasad, M. Savvides, Gait-ID on the move: Pace independent human Identification using cell phone accelerometer dynamics, IEEE Fifth Int'l Conf. on Biometrics: Theory, Applications and Systems (BTAS), pp. 8-15, 2012.

Thong, Y. and Deng, Y., Sep. 2014. Sensor orientation invariant mobile gait biometrics. In Biometrics (IJCB), 2014 IEEE International Joint Conference on (pp. 1-8). IEEE.
K. Altun and B. Barshan. "Human activity recognition using inertial/magnetic sensor units." In Human Behavior Understanding, pp. 38-51. Springer Berlin Heidelberg, 2010.
K. Aminian, B. Najafi, C. Büla, P-F. Leyvraz, and P. Robert. "Spatio-temporal parameters of gait measured by an ambulatory system using miniature gyroscopes." Journal of biomechanics 35, No. 5 (2002): 689-699.
D. Anguita, A. Ghio,. Oneto, X. Parra and J. L. Reyes-Ortiz. Human Activity Recognition on Smartphones using a Multiclass Hardware-Friendly Support Vector Machine. International Workshop of Ambient Assisted Living (IWAAL 2012). Vitoria-Gasteiz, Spain. Dec. 2012.
D. Anguita, A. Ghio, L. Oneto, X. Parra, and J. L. Reyes-Ortiz. "Energy efficient smartphone-based activity recognition asing fixed-point arithmetic." J. Univ. Comput. Sci 19 (2013): 1295-1314.
D. Anguita, A. Ghio, L. Oneto, X. Parra, and J. L. Reyes-Ortiz, A public domain dataset for human activity recognition using smartphones. In European Symposium on Artificial Neural Networks, Computational Intelligence and Machine Learning, ESANN. (Dec. 2013).
A. Avci, S. Bosch, M. Marin-Perianu, R. Marin-Perianu, and P. Havinga. "Activity recognition using inertial sensing for healthcare, wellbeing and sports applications: A survey." In Architecture of computing systems (ARCS), 2010 23rd International conference on, pp. 1-10. VDE, 2010.
L. Bao, and S. Intille. Activity recognition from user-annotated acceleration data. In Pervasive Computing, pp. 1-17. Springer Berlin Heidelberg, 2004.
N. F. Butte, U. Ekelund, and K. R. Westerterp. "Assessing physical activity using wearable monitors: measures of physical activity." Medicine and science in sports and exercise 44.1 Suppl 1 (2012): S5-12.
A. G. Cutti, A. Ferrari, P. Garofalo, M. Raggi, A. Cappello, and A. Ferrari. "'Outwalk': a protocol for clinical gait analysis based on inertial and magnetic sensors." Medical & biological engineering & computing 48, No. 1 (2010): 17-25.
M. O. Derawi. Accelerometer-based gait analysis, a survey. In Norwegian Information Security Conference (NISK), pp. 33-44, 2010.
M.O. Derawi, C. Nickel, P. Bours, and C. Busch, Unobtrusive User-Authentication on Mobile Phones Using Biometric Gait Recognition, Sixth Int'l Conf. on Intelligent Information Hiding and Multimedia Signal Processing (IIH-MSP), pp. 306-311, 2010.
D. Gafurov, K. Helkala, and T. Sondrol. Biometric gait authentication using accelerometer sensor. JCP, 1(7):51-59, 2006.
D.Gafurov, E Snekkenes, Towardsunderstanding the uniqueness of gait biometric, 8th Int'l Conf. Automatic Face & Gesture Recognition, pp. 1-8, 2008.
A. K. Jain, S. Pankanti, S. Prabhakar, L. Hong, and A. Ross, Biometrics: a grand challenge, Proc. Int'l Conf. on Pattern Recognition, vol. 2, pp. 935-942, 2004.
A. K. Jain, D. Zongker, Feature selection: evaluation, application, and small sample performance, IEEE Trans. Pattern Analysis and Machine Intelligence, 19(2):153-158, 1997.
J. M. Jasiewicz, J. Allum, J. W. Middleton, A. Barriskill, P. Condie, B. Purcell, and R. Che Tin Li. "Gait event detection using linear accelerometers or angular velocity transducers in able-bodied and spinal-cord injured individuals." Gait & Posture 24, No. 4 (2006): 502-509.
T. Kobayashi, K. Hasida, and N. Otsu. Rotation invariant feature extraction from 3-d acceleration signals. In Int'l Conf. on Acoustics, Speech, and Signal Processing, pp. 3684-3687, 2011.
J.R. Kwapisz, G. M. Weiss, and S. A. Moore. Cell phone-based biometric identification. Biometrics: 4th IEEE Int'l Conf. Theory Applications and Systems (BTAS), 2010.

* cited by examiner

SENSOR PLACEMENT
FIG. 1

ALTERNATIVE ROTATION REPRESENTATION
FIG. 2

GAIT DYNAMICS IMAGE
FIG. 4

500

505                                   510

515                                   520

GDIS FOR MULTIPLE SUBJECTS
FIG. 5

FLOW CHART
FIG. 6

METHOD FOR SENSOR ORIENTATION INVARIANT GAIT ANALYSIS USING GYROSCOPES

RELATED APPLICATIONS

This application claims the benefit of U.S. Provisional Application No. 62/055,267, filed: 25 Sep. 2014. This application is herein incorporated by reference in its entirety for all purposes.

STATEMENT OF GOVERNMENT INTEREST

This invention was made with United States Government support under Contract No. FA8750-13-C-0225 awarded by the U.S. Department of the Air Force. The United States Government has certain rights in this invention.

FIELD OF THE INVENTION

The invention is related to sensors and more particularly to the use of sensors for gait analysis.

BACKGROUND OF THE INVENTION

Recent advancement in inertial sensor technology has enabled high performing and low cost accelerometer and gyroscope sensors. An accelerometer sensor measures proper linear acceleration while a gyroscope sensor measures angular rotation or rotation rate. The linear acceleration and rotation measurements complement each other, and when they are combined, it is possible to recover the full sensor motion for tracking and navigation purposes.

When worn by a human body, accelerometers and gyroscopes enable direct and non-intrusive body motion data collection that can be used for gait and activity analysis. With the growing popularity and strong demands in smart mobile devices such as smart phones, smart watches, etc., there is a huge potential in motion analysis using the embedded accelerometer and gyroscope sensors for gait biometrics and activity recognition applications.

Motion analysis using accelerometers for gait biometrics and activity recognition has been an active research area for the past decade. More recently, the use of gyroscopes has also been explored in addition to accelerometers as well. However, despite the surge in research efforts, the practical application of these sensors for gait analysis remains a challenge due to data dependency on sensor placement: the accelerations or rotations are measured along the sensor axis. These measurements change with sensor orientation even when body motion stays the same. Most existing research is conducted in fixed laboratory settings with restricted sensor placement to bypass this problem, and is vulnerable in real world usage where the placement of mobile devices is casual and even arbitrary. Although promising performance has been reported in well-controlled studies using accelerometers and gyroscopes, there is still a large gap between existing research and real world applications.

What is needed is an improved way to handle variation in sensor orientation and address variations in sensor placement for the purpose of gait biometric and activity recognition.

SUMMARY OF THE INVENTION data comprising obtaining, from at least one gyroscope, at least one pair of raw data An embodiment provides a method for invariant gait analysis using gyroscope measurements; obtaining, from the at least one pair of raw data measurements, at least two 3D rotation vectors; obtaining, from the at least one gyroscope, at least a second pair of raw data measurements; obtaining, from the at least a second pair of raw data measurements, at least a second set of two 3D rotation vectors; determining, from the at least two 3D rotation vectors and the at least a second set of two 3D rotation vectors, Gait Dynamics Images (GDIs); determining sequences by matching features of the GDIs to sequences; and outputting identification and or classification of features from the determined sequences, whereby the pairs of raw measurements are used to factor out orientation, providing a motion representation which is both invariant to sensor orientation changes and highly discriminative, thereby providing high-performance gait analysis. In embodiments, the at least one gyroscope comprises a second gyroscope, wherein the at least a second pair of raw data measurements is obtained from the second gyroscope. In other embodiments, the 3D rotation vectors are rotation rate or rotation angle integrated over a fixed-length time interval. In subsequent embodiments, the GDI is a generalized GDI through applying a linear operator to the raw data measurements. Additional embodiments comprise a pair of motion vectors from times t1 and t2. In another embodiment, the features comprise entries and or rows and or columns of the GDI images and features derived from the GDIs. For a following embodiment, inertial measurement comprises Direction Cosine Matrix (DCM) Inertial Measurement Unit (IMU) theory, wherein measurement intervals comprise a small time dt. In subsequent embodiments, an inner product between a pair of the 3D rotation axis vectors is invariant to sensor rotation. In additional embodiments the GDIs encode both dynamics for a time series and local interactions. In ensuing embodiments, quaternions are computed to represent rotation changes. In included embodiments, a 3D rotation is represented using three Euler angles. In yet further embodiments, 3D rotation is alternatively represented using a rotation axis vector and a rotation angle around an axis. In related embodiments, a first row of an inner product GDI image are inner products of observation pairs with time lag zero. For further embodiments, remaining rows contain interactions at varying time lags that contribute to additional discriminating information of gait dynamics.

Another embodiment provides a device for invariant gait analysis comprising providing at least one gyroscope; obtaining, from the at least one gyroscope, at least a first pair of raw data measurements; obtaining, from the at least a first pair of raw data measurements, at least two 3d rotation vectors; obtaining, from the at least one gyroscope, at least a second pair of raw data measurements; obtaining, from the at least a second pair of raw data measurements, at least a second set of two 3D rotation vectors; determining, from the at least two 3D rotation vectors and the at least a second set of two 3D rotation vectors, Gait Dynamics Images (GDIs); determining sequences by matching corresponding images of the GDIs to sequences; and outputting gait biometrics and or activity classification. For yet further embodiments, the at least one gyroscope is a three-axis gyroscope measuring rotation rate along three orthogonal axes of the gyroscope. For more embodiments, the at least one pair of raw data measurements and the at least a second pair of raw data measurements are measured at arbitrary locations. In continued embodiments, measurements taken from the at least one gyroscope are sampled at regular time intervals. For additional embodiments, the regular time intervals are longer than an average gait cycle and may depend on application, whereby all contexts within a gait cycle when computing GDIs are preserved.

A yet further embodiment provides a system for invariant gait analysis comprising providing one or two three-axis gyroscopes; obtaining, from the one or two gyroscopes, at least one pair of raw data measurements; obtaining, from the at least one pair of raw data measurements, at least two 3D rotation vectors; obtaining, from the one or two gyroscopes, at least a second pair of raw data measurements; obtaining, from the at least a second pair of raw data measurements, at least a second set of two 3D rotation vectors; determining, from the at least two 3D rotation vectors and the at least a second set of two 3D rotation vectors, Gait Dynamics Images (GDIs), wherein the 3D rotation vectors are rotation angle integrated over a fixed-length time interval, the time interval being longer than an average gait cycle, whereby all contexts within a gait cycle when computing GDIs are preserved; determining sequences by matching corresponding images of the GDIs to sequences; and outputting gait biometrics and activity classification, whereby the pairs of raw data measurements are used to factor out orientation, providing a motion representation which is both invariant to sensor orientation changes and highly discriminative, thereby providing high-performance gait analysis for biometric authentication, activity monitoring, and fall prediction.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

DETAILED DESCRIPTION

According to one embodiment of the invention, a gait representation for gyroscope data is provided. Pairs of raw measurements are used to factor out sensor orientation, which results in a motion representation which is both invariant to sensor orientation changes and highly discriminative to enable high-performance gait analysis.

Figure 1:
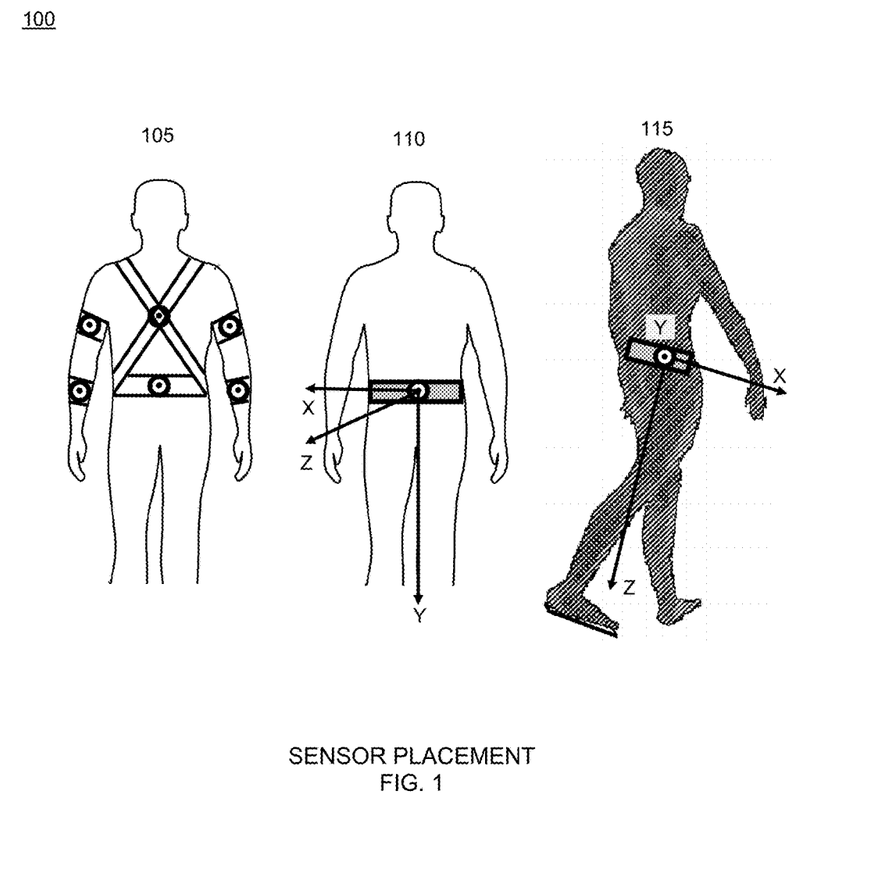
FIG. 1 shows multiple or single dedicated sensor(s) attached at fixed body positions configured in accordance with an embodiment of the invention.

FIG. 1 100 shows multiple 105, or single dedicated sensor(s) 110, 115 attached at fixed body positions with specific coordinate systems for the accelerometer due to data dependency on sensor placement. There has been increasing interest in the use of off-the-shelf mobile devices for gait biometrics. However, the phones still need to be carefully placed in a specific way to ensure consistent sensor orientation. Embodiments support these placements while providing invariant gait analysis. In other words, sensor orientation invariant gait analysis supports casual sensor placement.

Figure 2:
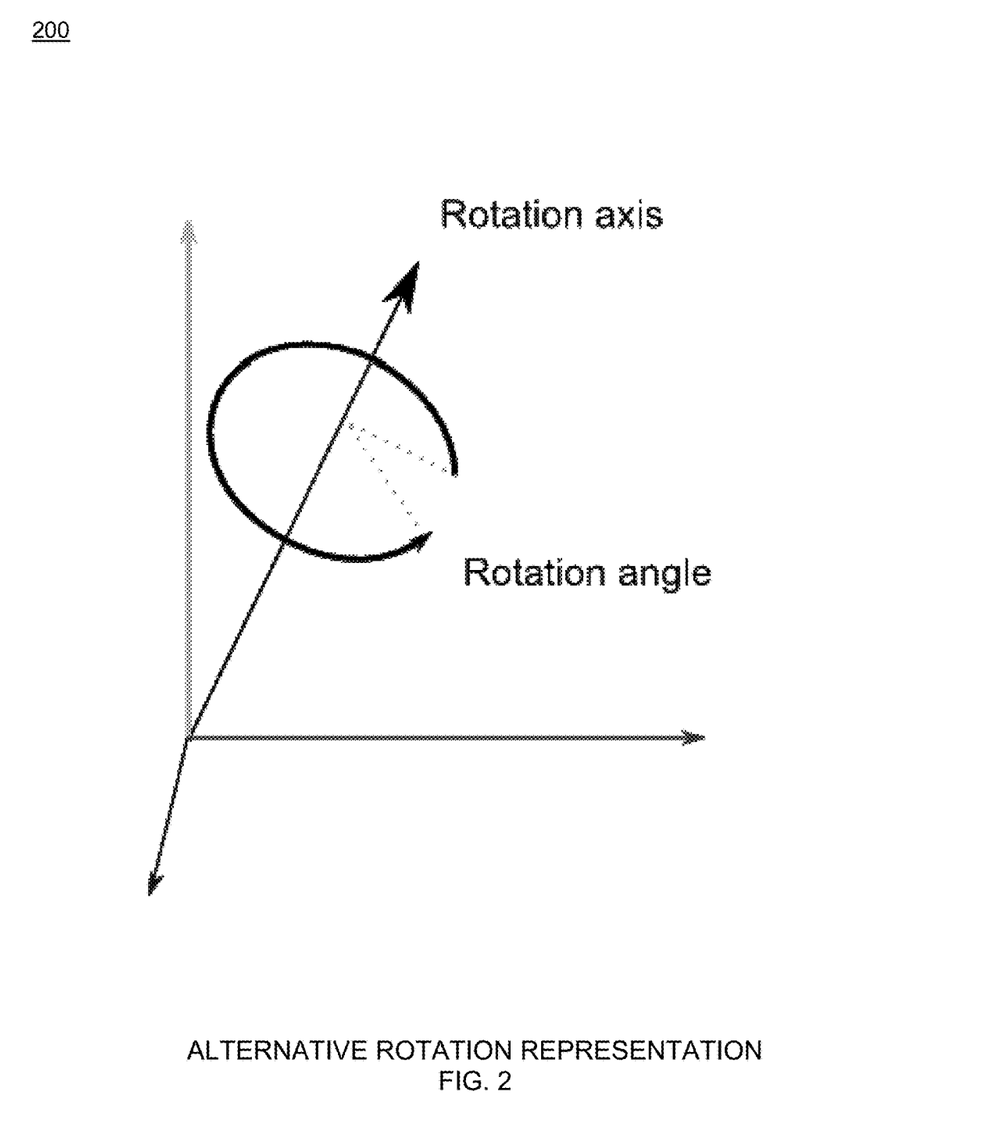
FIG. 2 shows an alternative rotation representation configured in accordance with one embodiment of the present invention.

FIG. 2 is a graph 200 showing an alternative rotation representation.

Figure 3:
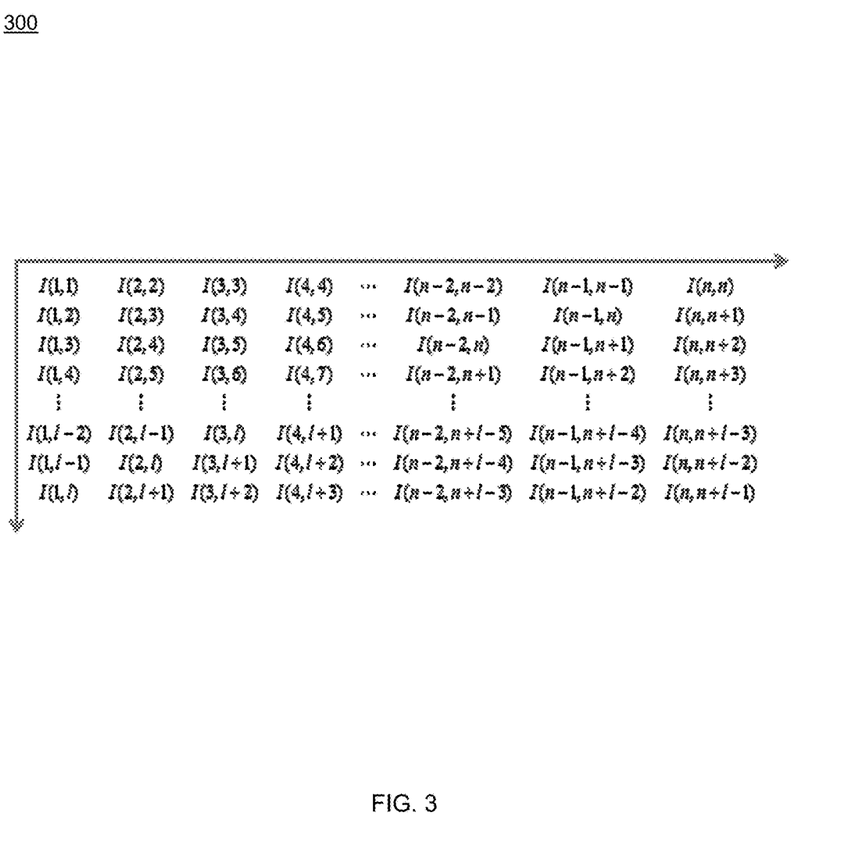
FIG. 3 shows the defining of Gait Dynamics Images (GDI) to characterize flow dynamics configured in accordance with one embodiment of the present invention.

FIG. 3 shows the defining of Gait Dynamics Images (GDI) 300 to characterize flow dynamics over time and interactions within each gait cycle that is robust to the placement of the gyroscope sensors.

Figure 4:
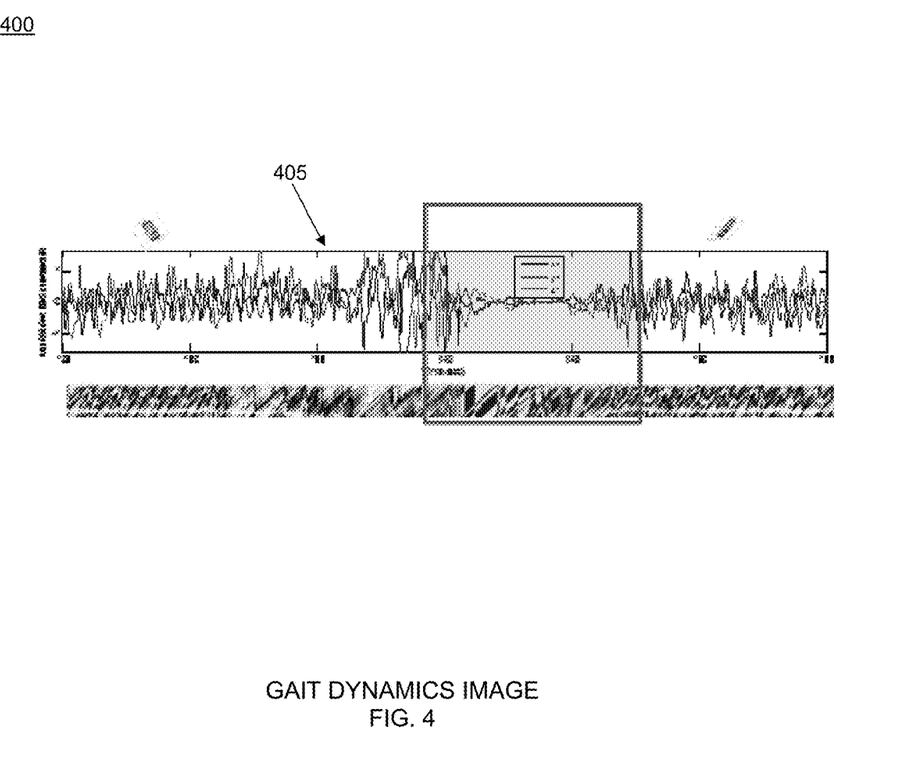
FIG. 4 shows Gait Dynamics Images for a 3D rate gyro sequence undergoing sensor orientation transition configured in accordance with one embodiment of the present invention.

FIG. 4 shows Gait Dynamics Image 400 for a 3D rate gyro sequence undergoing sensor orientation transition. Top: raw 3D gyro time sequence, bottom: corresponding GDIs 405. Note that while the raw signals become drastically different after the sensor orientation change, their corresponding GDI exhibits remarkable resemblance before and after the sensor orientation change.

Figure 5:
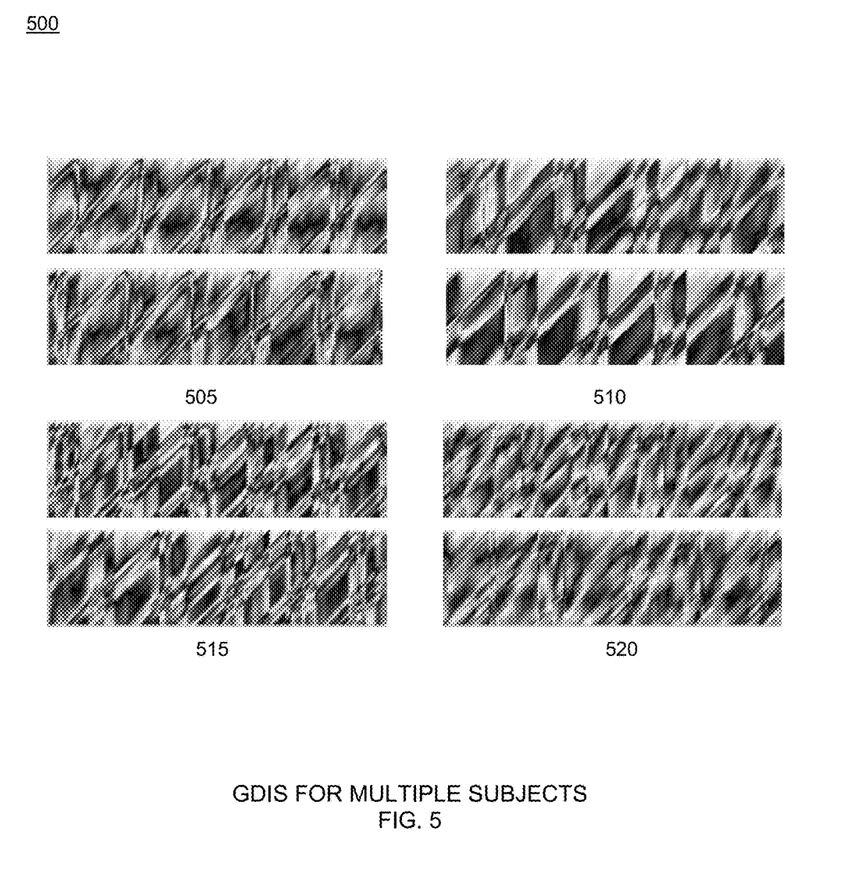
FIG. 5 shows GDIs obtained for multiple subjects configured in accordance with one embodiment of the present invention.

FIG. 5 shows GDIs 500 obtained for multiple subjects 505, 510, 515, and 520.

Figure 6:
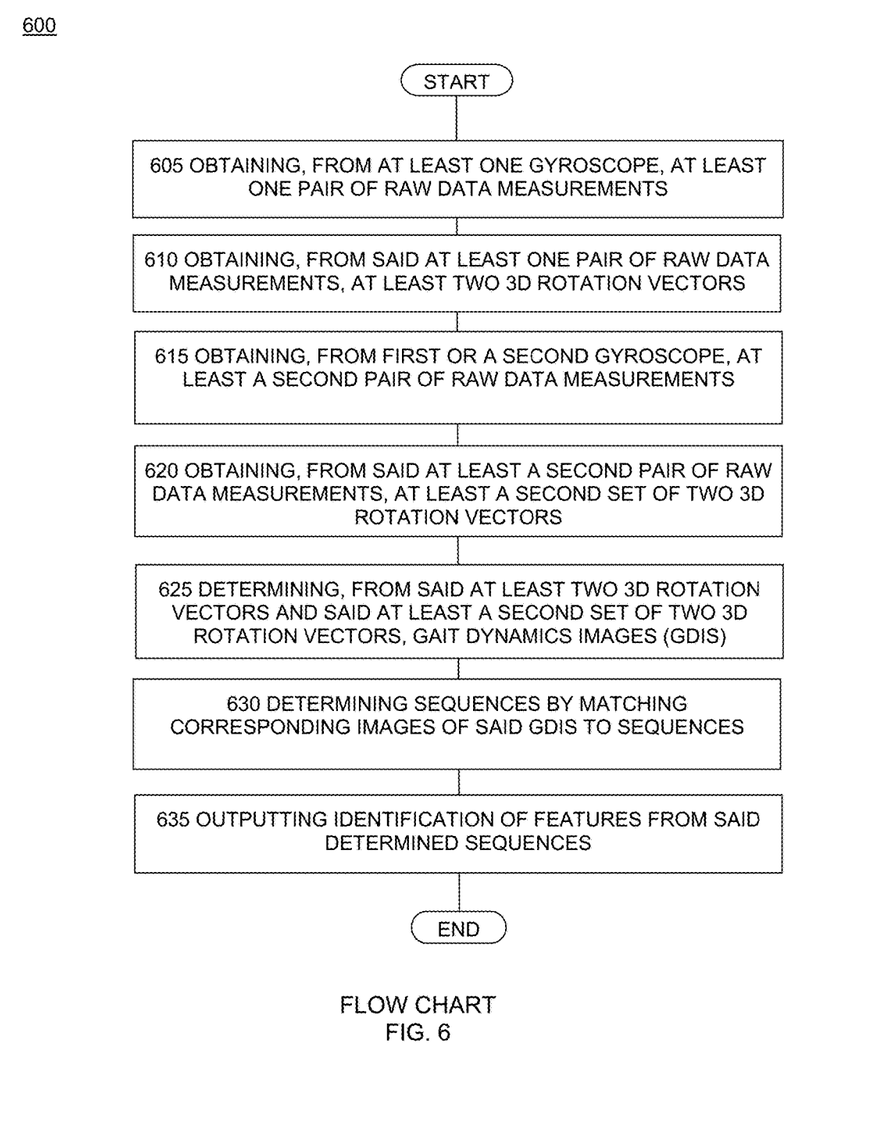
FIG. 6 is a method flow chart configured in accordance with one embodiment of the present invention.

FIG. 6 is a method flow chart 600. Steps comprise obtaining, from at least one gyroscope, at least one pair of raw data measurements 605; obtaining, from said at least one pair of raw data measurements, at least two 3D rotation vectors 610; obtaining, from either at least a second gyroscope, at least a second pair of raw data measurements, or at least a second pair of raw data measurements taken by the same (first) gyroscope at a different time (for example, the data captured today may be matched to the data captured a day before by the same gyroscope) 615; obtaining, from said at least a second pair of raw data measurements, at least a second set of two 3D rotation vectors 620; determining, from said at least two 3D rotation vectors and said at least a second set of two 3D rotation vectors, Gait Dynamics Images (GDIs) 625; determining sequences by matching corresponding images of said GDIs to sequences 630; and outputting identification of features from said determined sequences 635, whereby said pairs of raw measurements are used to factor out orientation, providing a motion representation which is both invariant to sensor orientation changes and highly discriminative, thereby providing high-performance gait analysis.

The most commonly used 3-axis gyroscopes measure rotation rate along three orthogonal axes of the sensor. As a result, the measurements vary depending on the sensor orientation, even when the external motion to be measured stays the same. In real world mobile device related applications where the sensor placement is less constrained, it becomes challenging to perform meaningful comparison of data features when data dependency on sensor placement is present.

This challenge of variations in sensor placement is approached by extracting motion features that characterize the distinguishing locomotion signature while at the same time staying invariant to sensor placement. Although the individual rotation data depends on sensor placement, it is possible to extract relationships between a pair of the observations from one sensor that do not. Subsequently, features can be computed using these pairwise interactions within a time interval to capture the local spatial-temporal motion dynamics, resulting in discriminative motion representations for robust gait analysis for gait biometrics and activity classification applications.

Orientation Invariant Gait Features

Let two 3D rotation vectors at times $t_1$ and $t_2$ be $\vec{r}(t_1)=[r_x(t_1)\ r_y(t_1)\ r_z(t_1)]^T$ and $\vec{r}(t_2)=[r_x(t_2)\ r_y(t_2)\ r_z(t_2)]^T$ by a sensor with a reference frame OXYZ. These rotation vectors may be rotation rate, or rotation angle integrated over a fixed length time interval using the rotation rate, or a rotation angle w.r.t a certain reference coordinate system. Let the corresponding rotation matrices be $\mathcal{R}(t_1)$ and $\mathcal{R}(t_2)$. These rotations are also measured by a second sensor with a reference frame OX'Y'Z': $\vec{r}'(t_1)=[r_x'(t_1)\ r_y'(t_1)\ r_z'(t_1)]^T$ and $\vec{r}'(t_2)=[r_x'(t_2)\ r_y'(t_2)\ r_z'(t_2)]^T$ and the corresponding rotation matrices are $\mathcal{R}'(t_1)$ and $\mathcal{R}'(t_2)$. Let the rotation between the two sensors be R. We have $\mathcal{R}'(t_1)=\mathcal{R}\mathcal{R}(t_1)$ and $\mathcal{R}'(t_2)=\mathcal{R}\mathcal{R}(t_2)$. The change in rotation is invariant to sensor placement: $\mathcal{R}'(t_2)^{-1}\mathcal{R}'(t_1)=\mathcal{R}^{-1}(t_2)\mathcal{R}^{-1}R\mathcal{R}(t_1)=\mathcal{R}^{-1}(t_2)\mathcal{R}(t_1)$. Either 3D rotation vectors or quaternions can be computed to represent the rotation changes. GDIs are then constructed using the rotation invariants.

Instead of using 3D rotation matrix or 3 Euler angles, a 3D rotation can alternatively be represented using a 3D rotation vector $\vec{u}(t)$ a rotation about the rotation axis $\vec{u}(t)$ by a rotation angle $\theta(t)=\|\vec{u}(t)\|$ (see FIG. 2). With this rotation representation, the magnitude of the rotation angle (or rotation rate) $\theta(t)$ at time t is invariant to the choice of reference coordinate system. The rotation axis $\vec{u}(t)$ at time t, on the other hand, depends on the reference frame. However, reference invariant features can be extracted using a pair of rotations (or rotation rates) $\vec{u}(t_1)$ and $\vec{u}(t_2)$ obtained at time $t_1$ and $t_2$ as shown in FIG. 2.

Given two 3D rotation (or rotation rate) axis vectors at times $t_1$ and $t_2$, with measurements and $\vec{u}(t_1)=[x(t_1)\ y(t_1)\ z(t_2)]^T$ and $\vec{u}(t_2)=[x(t_2)\ y(t_2)\ z(t_2)]^T$ by a first gyroscope with reference frame OXYZ, assume the same rotations (rates) are also captured by a second gyroscope with a reference frame OX'Y'Z': $\vec{u}'(t_1)=[x'(t_1)\ y'(t_1)\ z'(t_1)]^T$ and $\vec{u}'(t_2)=[x'(t_2)\ y'(t_2)\ z'(t_2)]^T$. Let the rotation between the two sensors be R. We have $\vec{u}'(t_1)=R\vec{u}(t_1)$ and $\vec{u}'(t_2)=R\vec{u}(t_2)$. Although the raw rotation (rate) axes depend on the sensor orientation, we are able to extract orientation invariant features using a pair of motion vectors at times $t_1$ and $t_2$:

$$<\vec{u'(t_1)},\vec{u'(t_2)}> = <R\vec{u(t_1)},R\vec{u(t_2)}>$$
$$= \vec{u(t_2)}^T R^T R \vec{u(t_1)}$$
$$= \vec{u(t_2)}^T \vec{u(t_1)}$$
$$= <\vec{u(t_1)},\vec{u(t_2)}>$$

Equation 1

That is, although the rotation (or rotation rate) axes depend on the sensor orientation, the inner product between a pair of the 3D rotation axis vectors does not. We can thus define the inner product invariant to sensor rotation:

$$I(\vec{u(t_1)},\vec{u(t_2)})=<\vec{u(t_1)},\vec{u(t_2)}>$$

Equation 2

This invariant quantity is related to the projection of one rotation axis vector on the other, or the angle between the two axes, which stays the same regardless of the choice of the reference frame.

For the 3-axis rate gyroscopes, let $\vec{\omega}(t)=[\omega_x(t)\ \omega_y(t)\ \omega_z(t)]^T$ be the output of measured rotation rate about the x-, y-, z-axes expressed in rad/s. According to the theory on Direction Cosine Matrix (DCM) Inertial Measurement Unit (IMU), for a small time dt, the combination of three small rotations about axes x-, y-, z-characterized by angular rotation vectors, $\vec{\omega_x}(t)$, $\vec{\omega_y}(t)$, $\vec{\omega_z}(t)$, where $\vec{\omega_x}(t)=[\omega_x(t)\ 0\ 0]^T$, $\vec{\omega_y}(t)=[0\ \omega_y(t)\ 0]^T$, $\vec{\omega_z}(t)=[0\ 0\ \omega_z(t)]^T$, is approximately equivalent to one small simultaneous rotation characterized by angular rotation vector $\vec{\omega}(t)=[\omega_x(t)\ \omega_y(t)\ \omega_z(t)]^T$, i.e., a rotation around axis defined by $[\omega_x(t)\ \omega_y(t)\ \omega_z(t)]^T$, with an angle equals the magnitude $\|[\omega_x(t)\ \omega_y(t)\ \omega_z(t)]^T\|$.

It has been established above that the magnitude of $\vec{\omega}(t)$, which is the rotation angle around the 3D rotation axis, is invariant to sensor axis, and the inner product of a pair of $\vec{\omega}(t)$ is also invariant to sensor reference frame. Consequently, the invariant feature can be computed for a pair of angular rate readings $\vec{\omega}(t_1)=[\omega_x(t_1)\ \omega_y(t_1)\ \omega_z(t_1)]^T$ and $\vec{\omega}(t_2)=[\omega_x(t_2)\ \omega_y(t_2)\ \omega_z(t_2)]^T$ from gyroscopes:

$$I(t_1,t_2)=<\vec{\omega(t_1)},\vec{\omega(t_2)}>$$

Equation 3

In the special case when $t_1=t_2$, we have $I(t,t)=<\vec{\omega(t)},\vec{\omega(t)}>=\|\vec{\omega(t)}\|$ We can also extract normalized invariants:

$$I(t_1, t_2) = \frac{<\vec{\omega(t_1)}, \vec{\omega(t_2)}>}{\|\vec{\omega(t_1)}\|\|\vec{\omega(t_2)}\|}$$

Equation 4

Gait Dynamics Images for Gyroscope Data

These invariant motion interactions are exploited to extract features that characterize the locomotion dynamics and which are robust to variations in sensor placement. Given a 3D rotation rate time series of size n sampled at regular time intervals $[\vec{\omega(1)},\vec{\omega(2)},\vec{\omega(3)},\ldots,\vec{\omega(n-1)},\vec{\omega(n)}]$, we define a two dimensional matrix which we call Gait Dynamics Image (GDI) to capture invariant motion dynamics over time and interactions within each gait cycle. Let the invariant feature computed using data vectors $\vec{\omega}(t_1)$ and $\vec{\omega}(t_2)$ be $I(t_1, t_2)$, using Equation 1-Equation 4. The Gait Dynamics Image (GDI) is defined as follows:

$$GDI(t,j)=I(j,t+j-1),$$

Equation 5 t=1, ..., l and j=1, ..., n−l+1 where l is the range of the time delay for concerning pairwise motion interactions, for which we choose to encode context within a typical gait cycle.

Gait Dynamics Images encode rich dynamics and context information characterizing the unique gait of an individual. As shown in FIG. 3, the ith row of the GDI contains all pairwise interactions of time delay i−1 over time, while the jth column consists of interactions between the motion at time j and all its successors up to time lag l−1 to capture local context. In particular, the first row of the inner product GDI image, which are the inner products of observation pairs with time lag n, corresponds to the squared magnitude sequence. It is related to the magnitude of rotation angles around rotation axis over time. The remaining rows contain the interactions at varying time lags that contribute to additional discriminating information of the gait dynamics.

This makes GDIs extremely powerful representations for motion analysis. FIG. 4 shows the gait dynamics image for a 3D rate gyro time sequence undergoing sensor orientation change. As can be seen, the GDIs exhibit much better consistencies before and after sensor orientation change than the raw time series. GDIs encode both dynamics for the time series and the local interactions. With the irregularly periodic input locomotion time series, gait dynamics images also display quasi-periodicity in both the time and time lag domains with the period approximating the length of a gait cycle. As shown in the GDI image, when the time lag coincides with the length of the local gait cycle, the inner product (Equation 3) or normalized correlation (Equation 4) are high as the signals repeat themselves. This is reflected by horizontal lines of high similarity measurements in both GDIs, starting with the first row, repeating at the length of a gait cycle. Gait cycles can be estimated by fitting smooth horizontal curves across the image which maximizes the overall intensities. Due to the quasi-periodic nature of gait and the repetitive pattern in GDIs, l is set to be a little more than the length of average gait cycles to preserve all contexts within a gait cycle when computing GDIs. FIG. 5 shows GDIs obtained for multiple subjects as we can see that distinct patterns in GDIs for different human subjects.

Generalized Gait Dynamics Images

The above shows how to compute sensor orientation invariant features from raw gyroscope sensory data of rotation rates. It is noted that the invariant property in (Equation 3) and (Equation 4) holds not only for the raw 3D sensory sequence, but also for derived sequences by applying a linear operator to the raw sensory data. Such derived data variables include

| Linear Operator | Derived Quantity |
| --- | --- |
| integration | rotations |
| FFT | Fourier features |

Generalized GDIs can be computed by substituting $\vec{\omega}(t)$ in (Equation 3) and (Equation 4) with these derived variables and can be used for sensor orientation invariant motion analysis.

Motion Analysis Using GDIs

Once GDIs have been computed from the raw data sequences, sequences can then be matched by matching corresponding GDIs images. Existing feature extraction and matching approaches can be leveraged from the image processing domain. Rows, columns, or patches of GDIs can be used as features as well. We use a local patch correlation based similarity measure to match two GDIs. One of the GDIs is divided into adjacent but non-overlapping windows of about two gait cycles (2.4 sec). Each of the windows is correlated with the second GDI image. In the correlation coefficient array, we extract the dominant peak in every window of size of a gait cycle (1.2 sec). These coefficients are then sorted and the pth percentile point of the coefficient is used as the score between the window from the first GDI and the second GDI. We compute a score for every window in the first GDI. We use the qth percentile point of these scores as the similarity between the two GDIs. The nearest neighbor classifier is then used to assign the label or identification of the nearest training GDI to the test GDI. The choice of order statistics for similarity measurement helps against the noise in data.

Application Domains

Motion analysis using GDIs computed from gyroscope sensory data have many applications, including but not limiting to, gait biometrics for user recognition and authentication, motion-deficiency related patient diagnosis and rehabilitation, wellness monitoring, activity analysis, elderly care and rehabilitation, gesture analysis and recognition, interactive gaming, machine/human interface, and the like.

The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

What is claimed is:

1. A method for invariant gait analysis using gyroscope data comprising:
obtaining, from at least one gyroscope, at least one pair of raw data measurements;
obtaining, from said at least one pair of raw data measurements, at least two 3D rotation vectors;
obtaining, from said at least one gyroscope, at least a second pair of raw data measurements;
obtaining, from said at least a second pair of raw data measurements, at least a second set of two 3D rotation vectors;
determining, from said at least two 3D rotation vectors and said at least a second set of two 3D rotation vectors, Gait Dynamics Images (GDIs);
determining sequences by matching features of said GDIs to sequences; and
outputting identification and or classification of features from said determined sequences,
whereby said pairs of raw measurements are used to factor out orientation, providing a motion representation which is both invariant to sensor orientation changes and highly discriminative, thereby providing high-performance gait analysis.

2. The method of claim 1, wherein said at least one gyroscope comprises a second gyroscope, wherein said at least a second pair of raw data measurements is obtained from said second gyroscope.

3. The method of claim 1, wherein said 3D rotation vectors are rotation rate or rotation angle integrated over a fixed-length time interval.

4. The method of claim 1, wherein said GDI is a generalized GDI through applying a linear operator to said raw data measurements.

5. The method of claim 1, comprising a pair of motion vectors from times t1 and t2.

6. The method of claim 1 wherein said features comprise entries and or rows and or columns of said GDI images and features derived from said GDIs.

7. The method of claim 1, wherein inertial measurement comprises Direction Cosine Matrix (DCM) Inertial Measurement Unit (IMU) theory, wherein measurement intervals comprise a small time dt.

8. The method of claim 1, wherein an inner product between a pair of the 3D rotation axis vectors is invariant to sensor rotation.

9. The method of claim 1, wherein said GDIs encode both dynamics for a time series and local interactions.

10. The method of claim 1, wherein quaternions are computed to represent rotation changes.

11. The method of claim 1, wherein a 3D rotation is represented using three Euler angles.

12. The method of claim 1, wherein 3D rotation is alternatively represented using a rotation axis vector and a rotation angle around an axis.

13. The method of claim 1, wherein a first row of an inner product GDI image are inner products of observation pairs with time lag zero.

14. The method of claim 13, wherein remaining rows contain interactions at varying time lags that contribute to additional discriminating information of gait dynamics.

15. A device for invariant gait analysis comprising:
providing at least one gyroscope;
obtaining, from said at least one gyroscope, at least a first pair of raw data measurements;
obtaining, from said at least a first pair of raw data measurements, at least two 3d rotation vectors;
obtaining, from said at least one gyroscope, at least a second pair of raw data measurements;
obtaining, from said at least a second pair of raw data measurements, at least a second set of two 3D rotation vectors;
determining, from said at least two 3D rotation vectors and said at least a second set of two 3D rotation vectors, Gait Dynamics Images (GDIs);
determining sequences by matching corresponding images of said GDIs to sequences; and
outputting gait biometrics and or activity classification.

16. The device of claim 15, wherein said at least one gyroscope is a three-axis gyroscope measuring rotation rate along three orthogonal axes of said gyroscope.

17. The device of claim 15, wherein said at least one pair of raw data measurements and said at least a second pair of raw data measurements are measured at arbitrary locations.

18. The device of claim 15, wherein measurements taken from said at least one gyroscope are sampled at regular time intervals.

19. The device of claim 18, wherein said regular time intervals are longer than an average gait cycle and may depend on application, whereby all contexts within a gait cycle when computing GDIs are preserved.

20. A system for invariant gait analysis comprising:
providing one or two three-axis gyroscopes;
obtaining, from said one or two gyroscopes, at least one pair of raw data measurements;
obtaining, from said at least one pair of raw data measurements, at least two 3D rotation vectors;
obtaining, from said one or two gyroscopes, at least a second pair of raw data measurements;
obtaining, from said at least a second pair of raw data measurements, at least a second set of two 3D rotation vectors;
determining, from said at least two 3D rotation vectors and said at least a second set of two 3D rotation vectors, Gait Dynamics Images (GDIs), wherein said 3D rotation vectors are rotation angle integrated over a fixed-length time interval, said time interval being longer than an average gait cycle, whereby all contexts within a gait cycle when computing GDIs are preserved;
determining sequences by matching corresponding images of said GDIs to sequences; and
outputting gait biometrics and activity classification,
whereby said pairs of raw data measurements are used to factor out orientation, providing a motion representation which is both invariant to sensor orientation changes and highly discriminative, thereby providing high-performance gait analysis for biometric authentication, activity monitoring, and fall prediction.

* * * * *